United States Patent [19]
Nielsen

[11] 4,209,020
[45] Jun. 24, 1980

[54] ELECTRODE ASSEMBLY

[76] Inventor: R. Frederick Nielsen, P. O. Box 3404, Cherry Hill, N.J. 08034

[21] Appl. No.: 943,636

[22] Filed: Sep. 19, 1978

[51] Int. Cl.² ............................................. A61B 5/04
[52] U.S. Cl. ................................... 128/640; 128/641
[58] Field of Search ............................... 128/639–642, 128/644, 798, 802, 803

[56] References Cited
U.S. PATENT DOCUMENTS

| | | | |
|---|---|---|---|
| 3,977,392 | 8/1976 | Manley | 128/641 |
| 4,121,573 | 10/1978 | Crovella | 128/640 |

Primary Examiner—Lee S. Cohen
Attorney, Agent, or Firm—Duffield & Lehrer

[57] ABSTRACT

A disposable electrode assembly is comprised of a thin flexible foam pad of insulating material having an adhesive base which can be firmly secured to a patient. The base carries an electrode which is in electrical contact with the patient's skin when the assembly is secured to the patient. A plurality of input terminal connectors are carried by the pad and are adapted to be connected to a plurality of electrodes which may be applied to the scalp of a fetus or to other parts of a patient's body. Also carried by the pad is an output connector which, through a cable, is adapted to connect the electrode assembly to a fetal monitor or an electrocardiograph or similar device. The output connector is electrically connected to the input connectors and to the base electrode by conductors within the electrode assembly.

13 Claims, 8 Drawing Figures

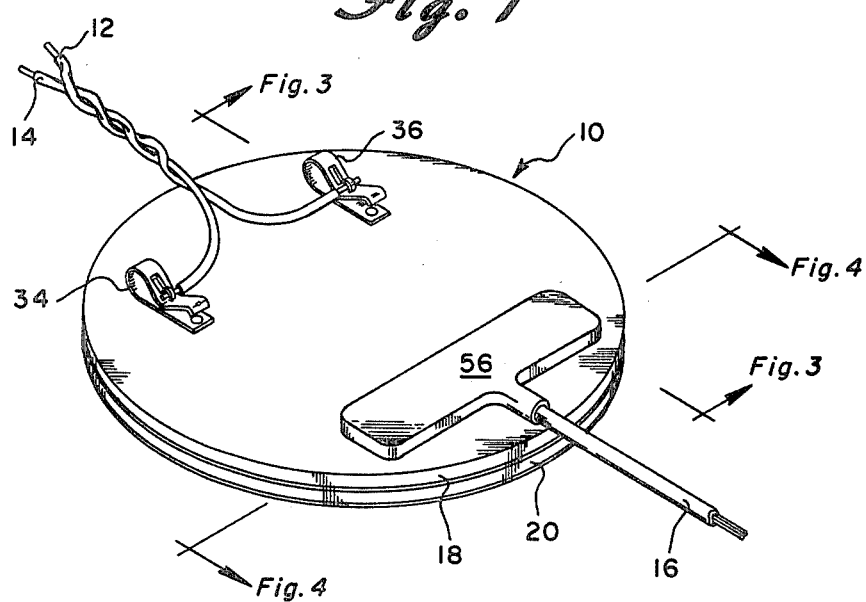
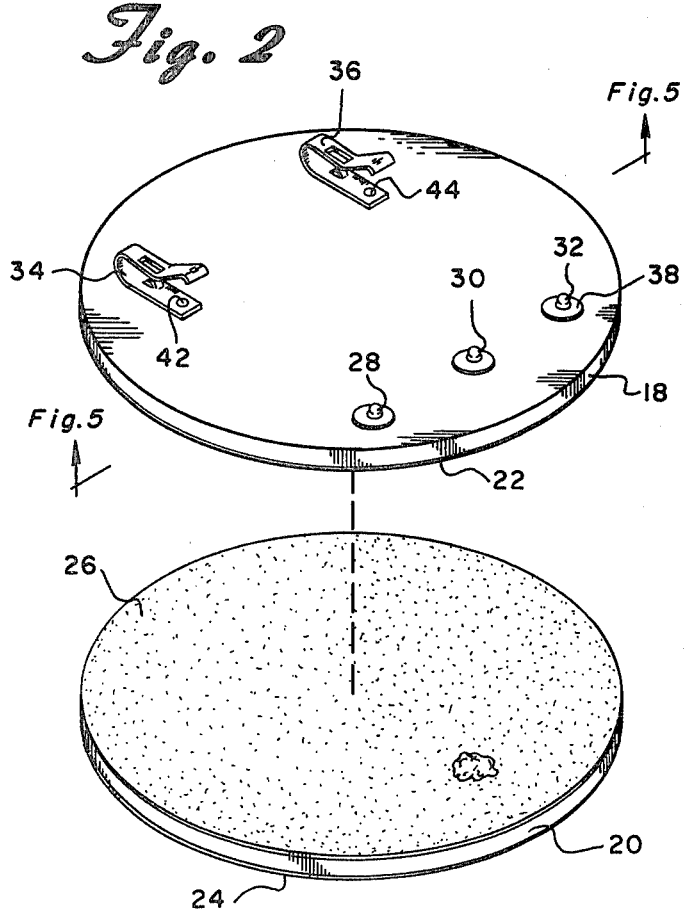

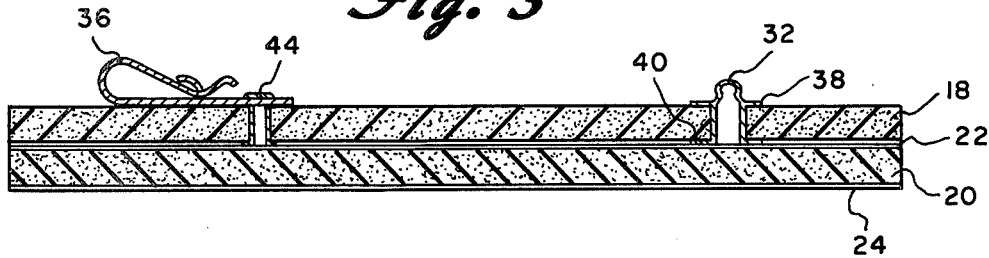
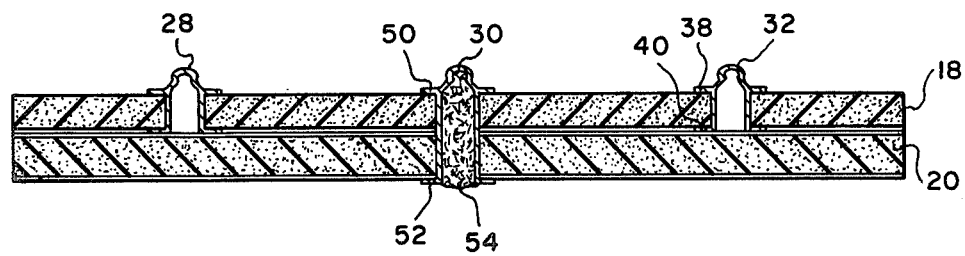
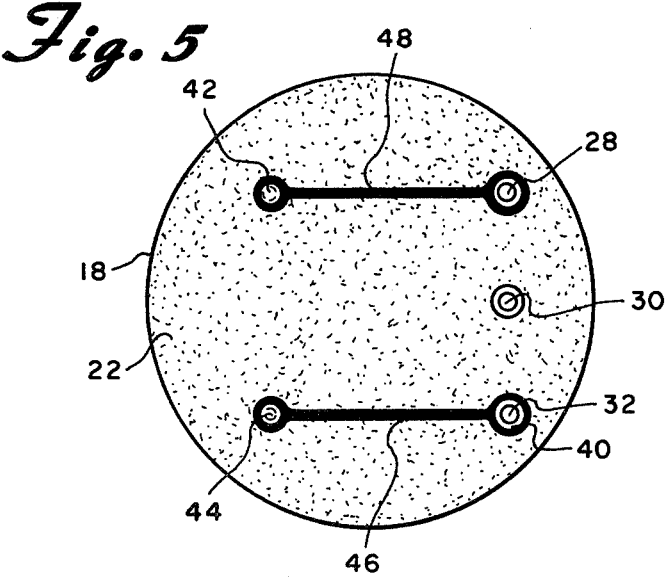
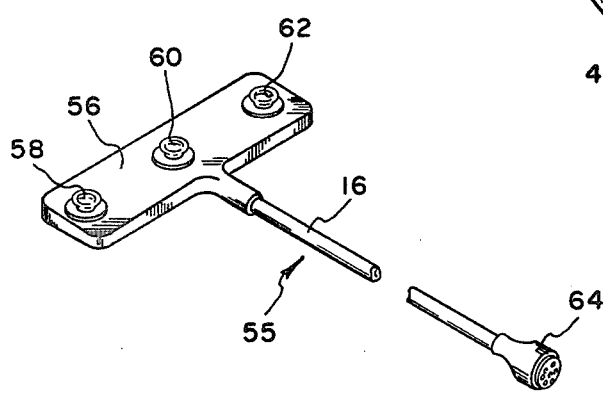

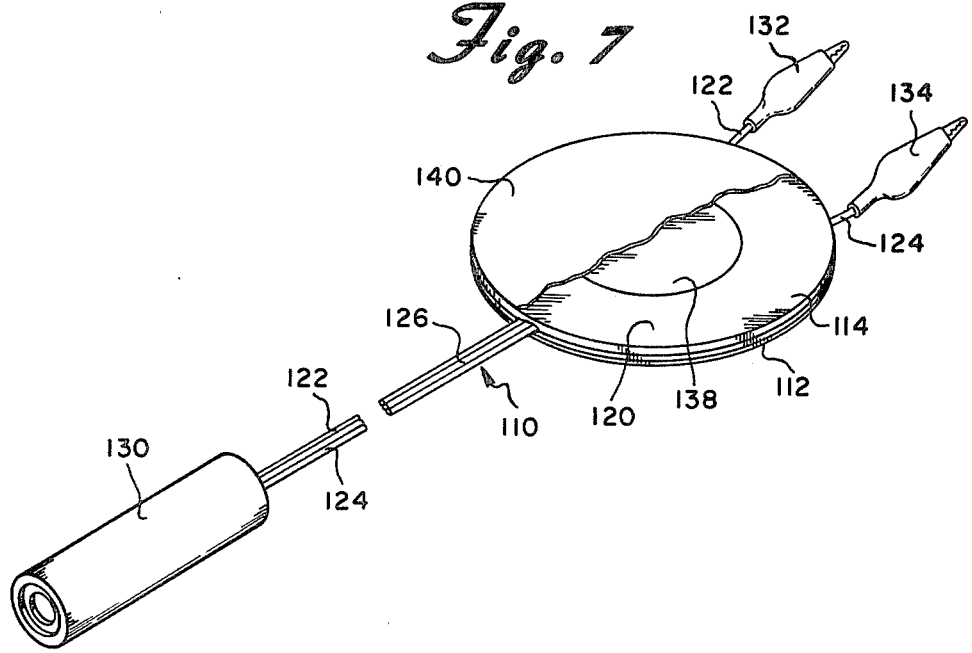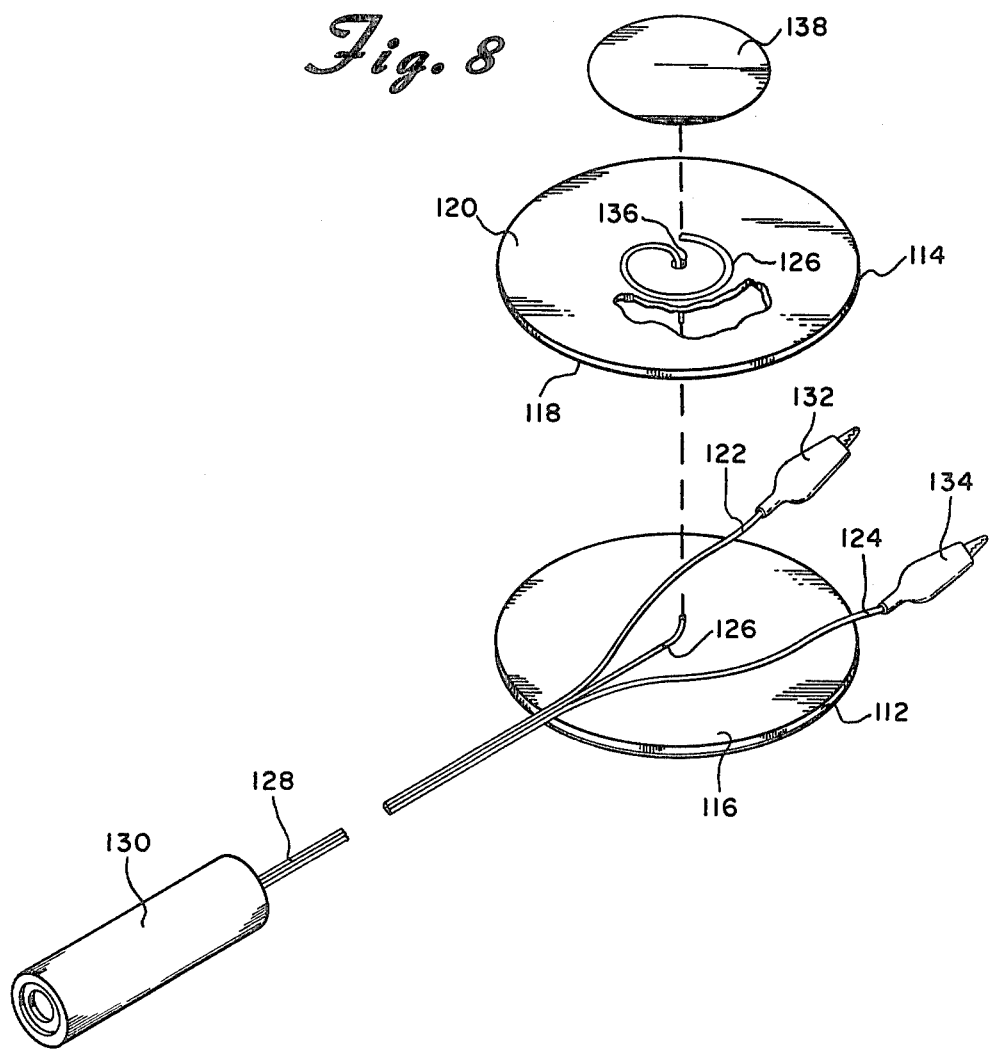

ELECTRODE ASSEMBLY

BACKGROUND OF THE INVENTION

This invention relates to an electrode assembly and more particularly to a disposable electrode assembly which is particularly useful as part of a fetal monitoring system.

Fetal monitoring is a technique which has been used for several years primarily during the time when a pregnant woman is in labor. This is accomplished by attaching one or more electrodes to the fetus' scalp. The electrodes are connected to a fetal monitoring device by wires passing through the birth chanal. An additional electrode is attached to the mother. This additional electrode is used to establish a base or reference voltage for the fetal electrodes.

In order to avoid accidentally dislodging the fetal electrodes, an electrode assembly has been used which is comprised of a metal base plate strapped to the mother's thigh. The plate carries a pair of connectors insulated therefrom which are adapted to be connected to the wires passing through the birth canal to the fetal electrodes. A main cable electrically connected to the metal base plate and to the connectors is used to connect the electrode assembly to the fetal monitoring device. This prevents movement of the fetal electrodes in the event that the mother moves relative to the fetal monitoring device.

While the above described electrode assembly has met with some success, it has several drawbacks. The most significant of which is its expense. The cost of such devices normally is between fifty and one hundred dollars and while they may be used numerous times, they represent a capital investment to a hospital which cannot be directly passed on to the patient. In addition, a hospital would require numerous identical devices since they become soiled during use and must be cleaned before being reused.

SUMMARY OF THE INVENTION

The present invention overcomes the problems of prior electrode assemblies known to applicant by providing an inexpensive disposable electrode assembly. The assembly is comprised of a thin flexible foam pad of insulating material having an adhesive base which can be firmly secured to a patient. The base carries an electrode which is in electrical contact with the patient's skin when the assembly is secured to the patient. A plurality of input connectors are carried by the pad and are adapted to be connected to a plurality of fetal electrodes. Also carried by the pad is an output connector which, through a cable, is adapted to connect the electrode assembly to a fetal monitor. The output connector is electrically connected to the input connectors and to the base electrode by conductors within said electrode assembly.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

FIG. 1 is a top perspective view of an electrode assembly constructed in accordance with the principles of the present invention;

FIG. 2 is an exploded view similar to FIG. 1;

FIG. 3 is a cross-sectional view taken along the line 3—3 of FIG. 1;

FIG. 4 is a cross-sectional view taken along the line 4—4 of FIG. 1;

FIG. 5 is a bottom plan view of the top layer of the assembly taken along the line 5—5 of FIG. 2;

FIG. 6 is a bottom perspective view of a cable adapted to connect the electrode assembly of the present invention to a fetal monitoring device;

FIG. 7 is a bottom perspective view of a second embodiment of the present invention, and FIG. 8 is an exploded view of the embodiment shown in FIG. 7 with portions broken away for clarity.

DETAILED DESCRIPTION OF THE PREFERRED EMBODIMENT

Referring now to the drawings in detail, wherein the like reference numerals have been used throughout the various figures to identify like elements, there is shown in FIG. 1 an electrode assembly constructed in accordance with the principles of the present invention and shown generally as 10. Electrode assembly 10 is shown in use with wires 12 and 14 connected thereto which lead to the fetal electrodes on the scalp of the fetus and with cable 16 connected to the fetal monitoring device.

As shown most clearly in FIGS. 2, 3 and 4, the electrode assembly is comprised essentially of a pair of foam pads 18 and 20. By way of example and not limitation, the pads 18 and 20 may be circular in configuration with a diameter of approximately 2¼ inches and a thickness of 1/16 inch. The upper pad 18 has an adhesive material 22 on the bottom surface thereof. The lower pad 20 also has an adhesive material 24 on its lower surface and, in addition, preferably has an adhesive material 26 on its upper surface.

One side of the electrode assembly 10 carries a plurality of electrical output terminals or connectors. In the preferred embodiment, three connectors 28, 30 and 32 are shown. These connectors are the male portions of snap-on connectors which, per se, are well-known. The connectors 28, 30 and 32 extend upwardly from the top surface of the upper pad 18 so as to be accessible therefrom.

The other side of the electrode assembly 10 carries a plurality of electrical input terminals or connectors. In the preferred embodiment, two such connectors 34 and 36 are shown. In practice and for the reason which will become more readily apparent hereinafter, there will be one less input connector than output connectors.

As shown in FIGS. 3 and 4, connectors 28 and 32 pass through holes in upper pad 18 and are secured in place by outwardly extending flanges 38 and 40. Connectors 34 and 36 are connected to the upper pad 18 by way of metal rivots or the like 42 and 44.

As shown in FIG. 5, a flat conductor such as a metallic foil or the like 46 extends between flanges 38 of connector 32 and the rivot 44 of connector 36. A similar metallic foil 48 extends between the flange of connector 28 and the rivot 42. The conductors 46 and 48 are held in place by the above described flanges and rivots and by the adhesive material 22. It should therefore be readily apparent that the connector 28 is electrically connected to the connector 34 and the connector 32 is electrically connected to the connector 36. However, the connectors 28 and 34 on the one hand and 32 and 36 on the other are electrically insulated from each other and from the connector 30. In addition, when the lower pad 20 is applied to the lower surface of pad 18, the lower portions of the rivots, flanges and conductors 46 and 48 are covered and are thereby electrically insulated from anything below the electrode assembly 10.

Connector 30 differs from connectors 28 and 32 in that it passes through holes in both the upper pad 18 and the lower pad 20 as shown most clearly in FIG. 4. Connector 30 is secured in place by upper flange 50 and lower flange 52. The cavity in the center of the connector 30 may be, if desired, filled with a conductive paste which extends slightly beyond the lower portion thereof. The electrode assembly is completed by applying a wax or glossy paper material or the like to the bottom surface of pad 20. The paper covers the adhesive material 24 to prevent the same from accidentally adhering to other objects and it protects the paste 54 from drying out.

The electrode assembly 10 described above is used in the following manner. First, the paper or other protective coating on the bottom surface of the pad 20 is removed and the electrode assembly is pressed on to a person's body. If being used with a fetal monitoring device, the electrode assembly 10 would be adhered to the inside and upper portion of a woman's thigh. The electrode assembly is securely held in place by the adhesive 24 which preferably is of the non-allergic type. At the same time, the conductive paste 54 is forced into contact with the patient's skin and functions as a body electrode which is electrically connected to connector 30.

After the scalp electrodes are applied to the fetus' head, the wires 12 and 14 extending therefrom and passing through the birth canal are connected to the input connectors 34 and 36. The electrode assembly 10, therefore, functions not only as a body electrode itself but also as a support for the wires 12 and 14 leading to the scalp electrodes. Thus, all that is now needed are connections between the output connectors 28, 30 and 32 and the fetal monitoring device. This is accomplished by way of cable assembly 55 shown in FIG. 6.

Cable assembly 55 includes a first end 56 including a plurality of connectors 58, 60 and 62. Connectors 58, 60 and 62 are the female counterparts of the output connectors 28, 30 and 32 and are aligned therewith so that the end 56 of cable assembly 55 can be placed over the first side of the electrode assembly 10 and electrical connections can be made between the respective output connectors 28, 30 and 32 on the one hand and connectors 58, 60 and 62 on the other. This is shown in FIG. 1. The other end of cable assembly 55 carries a connector 64 which is adapted to cooperate with the fetal monitoring device. Cable 16 connects the two ends of the cable assembly 55 together.

A second embodiment of the electrode assembly is shown in FIGS. 7 and 8 and is designated generally as 110. Electrode assembly 110 also includes upper and lower foam pads 112 and 114. It should be noted that for purposes of an accurate description, the device of FIGS. 7 and 8 is shown upside down so that the upper pad is designated as 112 and the lower pad as 114.

Upper pad 112 has an adhesive material 116 on the lower surface thereof. Lower pad 114, however, preferably has adhesive material 118 and 120 on both surfaces thereof. Lying between the pads 112 and 114 are a plurality of insulated relatively thin wires or conductors 122, 124 and 126. Adjacent one edge of the pads 114 and 116, the three wires join together to form a single cable 128 which terminates in a multi terminal or conductor jack or the like 130.

Wires 122 and 124 pass entirely through the interface between the pads 112 and 114 making no electrical connection with anything therein. These wires 122 and 124 terminate in electrical connectors or terminals such as spring clips in the form of alligator clips 132 and 134, respectively. Wire 126, however, passes through hole 136 adjacent the center of lower pad 114 and is pressed against the adhesive 120 after the insulation is removed from that portion thereof extending through the hole 136. The end of wire 126 and the hole 136 are then covered by a thin piece of metal 138. Metal 138 which serves as a body electrode is held in place on the lower pad 114 and in electrical contact with the end of wire 126 by the adhesive 120. A protective paper cover 140 is then applied over the surface of the pad 114.

The electrode assembly 110 shown in FIGS. 7 and 8 is used in substantially the same manner as the electrode assembly 10 described above. The protective paper 140 is first removed and the lower surface of pad 114 with the adhesive 120 exposed is pressed on to the patient's body. The metal 138 is held tightly against the skin and functions as a body electrode which, through wire 126, is connected to the jack 130. The wires from the fetal electrodes are then connected to the alligator clips 132 and 134 and a cable from the fetal monitoring device is plugged into the jack 130.

It should be readily apparent that due to the relative simplicity of the electrode assemblies 10 and 110, they can be made relatively inexpensively. In this way, the electrode assemblies can be used once and then discarded.

While the invention has been described with specific reference for use with a fetal monitoring device, it should also be readily apparent that the invention may have numerous other uses. For example, the electrode assembly could be used with an electrocardiogram. In this way, the base or lower pad of the electrode assembly itself will function as one of the body electrodes and would also function as a support for wires leading to other electrodes placed on other parts of the patient's body. In this way, the number of wires leading to the electrocardiogram would be reduced to one main cable from the electrocardiogram to the electrode assembly of the present invention. It should also be noted that while two input and three output connectors are illustrated in the two embodiments of the present invention, this is by way of example only. It should be readily apparent that a greater or lesser number of connectors may be employed.

The present invention may be embodied in other specific forms without departing from the spirit or essential attributes thereof and, accordingly, reference should be made to the appended claims, rather than to the foregoing specification as indicating the scope of the invention.

I claim:

1. A disposable electrode assembly comprising:
  a thin flexible pad of insulating material, said pad having an adhesive means on one surface thereof for attaching the same to a person's body;
  a body electrode on said one surface of said pad, said body electrode being adapted to be in electrical contact with a person's body when said pad is attached thereto;
  input connector means adapted to be connected to remotely located electrode means to receive signals from said electrode means and output connector means adapted to be connected to an external device for delivering signals thereto, said input and output connector means being carried by said pad at a position remote from said one surface, and conductor means carried by said pad electrically interconnecting said input connector means to said output connector means and said output connector means to said body electrode.

2. A disposible electrode assembly as claimed in claim 1 wherein said pad is comprised of two layers adhered together and wherein at least part of said conductor means lies between said two layers.

3. A disposable electrode assembly as claimed in claim 1 wherein said body electrode is electrically connected to said output connector means by part of said conductor means passing through a hole in said pad.

4. A disposable electrode assembly as claimed in claim 1 wherein said body electrode is comprised of a conductive paste.

5. A disposable electrode assembly as claimed in claim 1 wherein said body electrode is comprised of a thin piece of metal.

6. A disposable electrode assembly as claimed in claim 1 wherein said input connector means is comprised of a plurality of individual connectors adapted to be connected to wires leading to said remotely located electrode means.

7. A disposable electrode assembly as claimed in claim 6 wherein said output connector means is comprised of a plurality of connectors, the number of output connectors being one greater than the number of input connectors.

8. A disposable electrode assembly as claimed in claim 1 wherein said input connector means is comprised of a plurality of spring clips electrically insulated from each other.

9. A disposable electrode assembly as claimed in claim 1 further including a cable assembly means adapted to connect said output connector means to electronic monitoring equipment.

10. A disposable electrode assembly as claimed in claim 1 wherein said input connector means is comprised of at least one electrical terminal and wherein said output connector means is comprised of multiple electrical terminals, the number of output terminals being one greater than the number of input terminals.

11. A disposable electrode assembly as claimed in claim 10 wherein said conductor means connects said body electrode to one of said output terminals.

12. A disposable electrode assembly as claimed in claim 11 wherein said at least one input terminal is comprised of a spring clip suspended from said pad by part of said conductor means.

13. A disposable electrode assembly as claimed in claim 12 wherein said output terminals are mounted together in a single connector means which is suspended from said pad by part of said conductor means.

* * * * *